United States Patent [19]

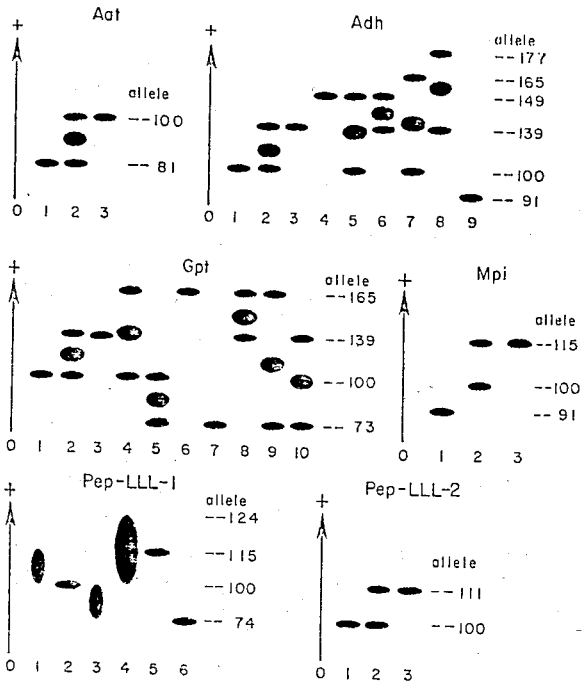
Aat
allele
--100
-- 81
0 1 2 3
Adh
allele
--177
--165
--149
--139
--100
-- 91
0 1 2 3 4 5 6 7 8 9
Gpt
allele
--165
--139
--100
-- 73
0 1 2 3 4 5 6 7 8 9 10
Mpi
allele
--115
--100
-- 91
0 1 2 3
Pep-LLL-1
allele
--124
--115
--100
-- 74
0 1 2 3 4 5 6
Pep-LLL-2
allele
--111
--100
0 1 2 3

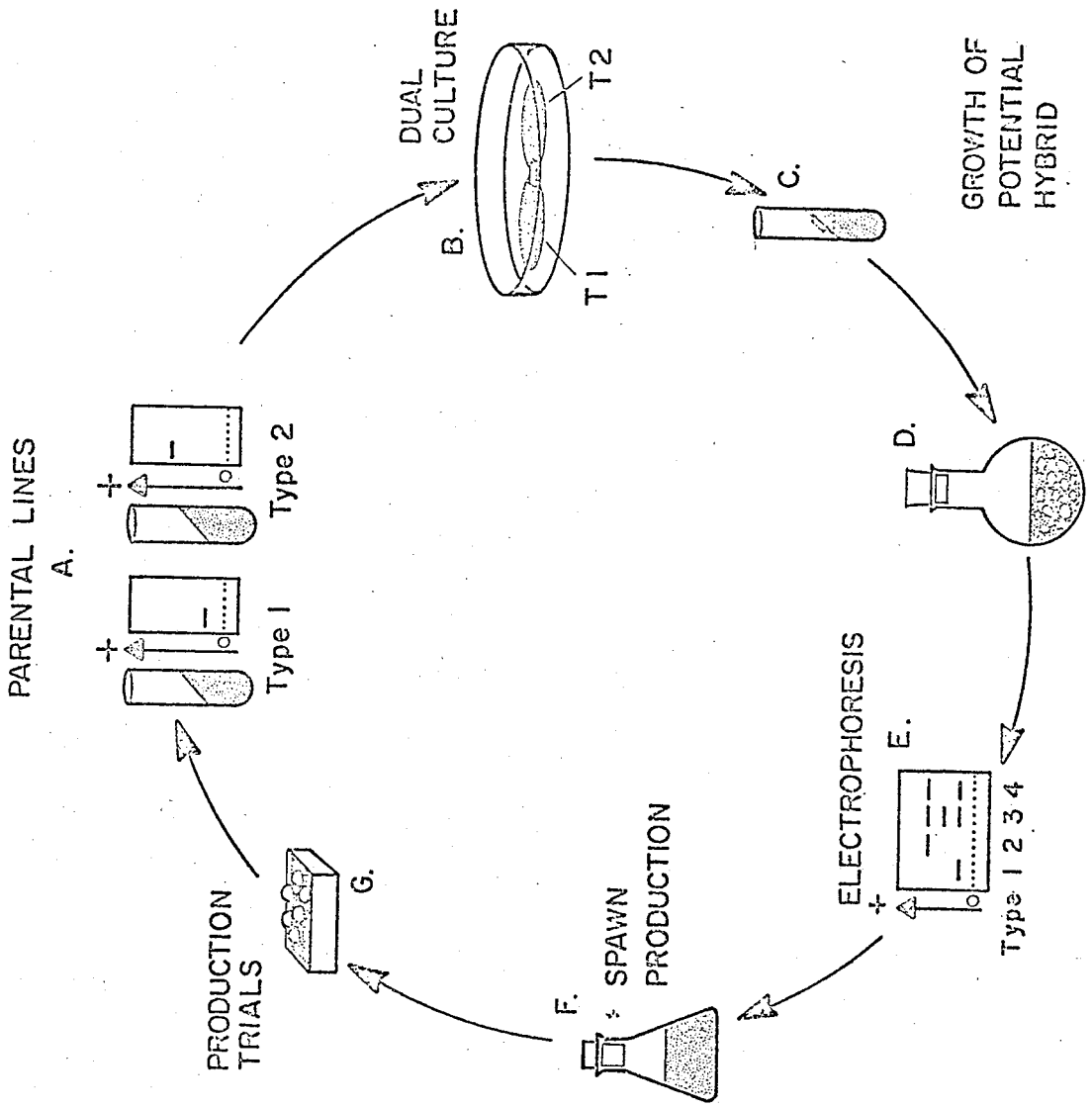
PARENTAL LINES
A.
Type 1
Type 2
B.
DUAL CULTURE
T1
T2
C.
GROWTH OF POTENTIAL HYBRID
D.
E.
ELECTROPHORESIS
Type 1 2 3 4
F.
SPAWN PRODUCTION
G.
PRODUCTION TRIALS

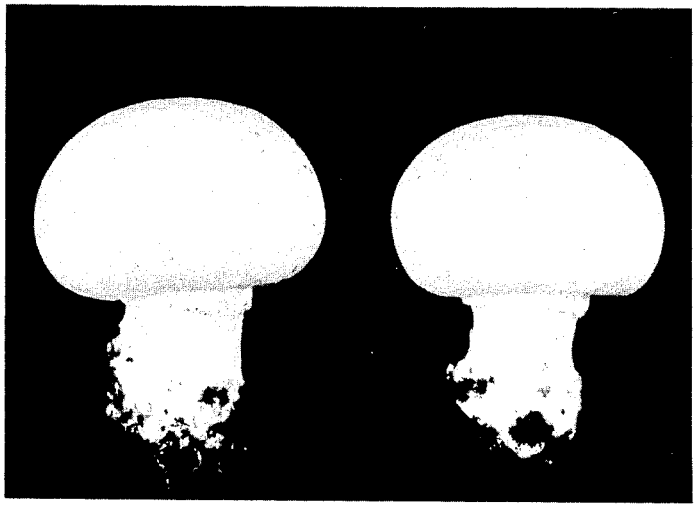

Royse et al.

[11] Patent Number: Plant 5,772

[45] Date of Patent: Jul. 22, 1986

[54] MUSHROOM PLANT

[75] Inventors: Daniel J. Royse, State College, Pa.; Bernard P. May, Groton, N.Y.

[73] Assignee: Research Corporation, New York, N.Y.

[21] Appl. No.: 663,098

[22] Filed: Oct. 19, 1984

[51] Int. Cl.[4] ..... A01H 15/00

[52] U.S. Cl. ..... Plt./89

[58] Field of Search ..... Plt./89

*Primary Examiner*—Robert E. Bagwill

*Attorney, Agent, or Firm*—Scully, Scott, Murphy & Presser

[57] ABSTRACT

A new and distinct variety of mushroom is described. This variety is similar to a type called "off-white" in the trade. The new variety possesses advantages of both productivity and yield when compared to two commercially available line 348 and Moonlite TM. The novel variety also displays a unique electrophoretic isozyme pattern.

4 Drawing Figures

1

The present invention relates to a new and distinct variety of mushroom plant of *Agaricus brunnescens* Peck [=*A. bisporus* (Lange) Imbach].

No other major commercially important crop has experienced as little genetic improvement as the common edible mushroom, *Agaricus brunnescens* Peck. [=*Agaricus bisporus* (Lange) Imbach]. This situation has been due exclusively to the unique genetic life history of this fungus which hinders and often precludes manipulation of the germ plasm without the use of specific codominant markers. Unlike other Agaricus spp., *Agaricus brunnescens* is primarily two-spored.

Selective breeding programs for *A. brunnescens* have been proposed which utilize auxotrophic mutants (Raper and Raper, *Mush. Sci.* 8:1-9 (1972)); Raper et al., *Mycologia* 64:1088-1172, (1972)), mycelial fusion and nuclear exchange between heterokaryotic lines (Moessner, *Mush. Sci.* 5:197-203 (1962)), multispore-derived cultures (Stubnya, *Mush. Sci.* 10(1); 83-89 (1979)), or resistance to biocides (Elliott, *Mush. Sci.* 10 (1):73-81 (1979)). Each of these approaches has the disadvantage that a limited number of crosses can be made, corroborated, and uniquely marked.

Isozyme analysis has proved to be a potent genetic tool because of the interpretable, one-to-one relationship of isozyme phenotype to the organism's genotype. The single-gene basis of observed electrophoretic variation in fungi by the use of single-spore-derived isolates has been shown for *Conidiobolus thromboides* Dreschler [syn, *Entomophthora virulenta* Hall et Dunn] (May et al. *Exp. Mycol* 3:289-297 (1979)), *Agaricus campestris* (May and Royse *Mush. Sci.* 11(2):799-817 (1981); and *Biochem. Genet.* 20:1165-1173, (1982)), and *A. brunnescens* (May and Royse supra (1981); and Royse and May *Mycologia* 74:93-102 (1982). For *A. brunnescens* isozyme analysis allows the ability to distinguish homokaryotic from heterokaryotic single-spore-derived lines.

On the basis of five variable biochemical loci Royse and May, (supra, 1982) were able to partition lines of *A. brunnescens* into genotypic classes. Combining the number of genotypes possible at each locus would allow over 20,000 recognizable genotypic classes. The finding of only five genotypic classes among 34 commercial lines and only 27 classes in 162 lines in The Pennsylvania State University Mushroom Culture Collection is further evidence that little of the potential genotypic variability is expressed in the stocks examined.

2

The novel variety described herein was produced as a result of the breeding program in the Department of Plant Pathology, The Pennsylvania State University. The invention was completed in two major phases: (1) crossing of two compatible breeding stocks (homokaryons) and (2) evaluation of desirable cultivation characteristics of the new hybrid. The new line was produced by crossing homokaryons derived from a golden white parent (232) commonly used in cave culture and a light cream parent (266) not commonly used for commercial cultivation. The improved characteristic of this mushroom line is its increased yield in $Kg/m^2$ as compared to the yield and size of the golden white variety (232).

The *A. brunnescens* isolates (232 and 266) were from The Pennsylvania State University Mushroom Culture Collection (PSUMCC). These lines have been electrophoretically typed by Royse and May (supra, 1982) and May and Royse (supra, 1982). Allelic variability represented in the PSUMCC is diagramatically represented in FIG. 1. The alleles for lines 232 and 266 at six biochemical loci are listed in Table 1.

Homokaryons were derived from lines 232 and 266 and used as breeding stock. The general scheme followed that presented in FIG. 2. The alleles for these homokaryons (232-58 and 266-324) are listed in Table 2. The cultures 232-58 and 266-324 were set up in dual culture as outlined by May and Royse (supra 1982). The alleles possessed by the resulting hybrid are listed in Table 3. The hybrid's allelic combination is unique to any commercial or PSUMCC isolates and can be easily distinguished from any of these isolates.

Evaluation of the hybrid's characteristics for commercial desirability were performed at the Mushroom Research Center of The Pennsylvania State University, University Park Pa. The hybrid was subjected to two (2) crop evaluations on two (2) different composts using commercial lines for comparisons. A summary of the results are presented in Tables 4 and 5. As can be seen from these tables, BB32 ($F_1$ hybrid) is generally superior in yield to the checks or commercial lines examined (Table 4). In both evaluations (Table 4) the novel line was significantly better than the Moonlite TM line. Yield for BB32 was also significantly higher than the commercial line (348) in crop 82-24 (Table 4). There was no significant difference in yield between 348 and BB32 for crop 82-18.

Mushroom size (Table 5) was significantly greater for BB32 than for the commercial line 348 for both crops. BB32 also was significantly larger than the commercial Moonlite TM line for crop 82–14, but there was no significant difference in size between these two lines for crops 82–18. In summary, the newly developed line has advantages in both size and yield when compared to two commercially used lines (348 and Moonlite TM).

Mushroom hybrid BB32 is of a type similar to one called "off-white" in the trade such as Darlington 11 or Darlington 76. The cap is scaly and "off-white" in color. Normally, this mushroom is colored an off-white and is moderately scaled; however, under drought conditions or relatively high air movement the caps are quite scaly and colored creamish-white. At maturity the cap frequently is domed. The caps and stalks of this mushroom are thicker than the typical "white" and "off-white" mushrooms.

The cap or pileus of the mushroom, when the veil breaks, varies between 25–150 mm in diameter and is of generally convex shape.

The stipe is 25–80 mm long, 8–25 mm thick, strongly bulbous in the button stage but becoming cylindrical at maturity.

The lamellae are whitish at first but become a pinkish flesh color by the time the veil breaks. Later the gills become a purplish brown and finally a chocolate brown as the spores mature. The gills are free, crowded, conspicuously white-marginate, with lamellae interspersed.

The annulus is prominent and fairly persistent, composed of a single type, formed from a velar sheath over the stipe extending up to the margin of the unexpanded pileus.

The flesh is white, turning bright pinkish red in approximately 2 min. when cut or bruised (particularly int the stipe) and later turning brown. The flesh is quite thick below the disc.

The pileus cuticle is composed of radially arranged, repent, parallel to interwoven, clampless, hyaline to creamish hyphae measuring 2.5–12 μm diameter. The pileus trama is composed of large, thin-walled, interwoven, clampless hyphae measuring 4–32 μm diameter. Pleurocystidia are lacking. Cheilocystidia are abundant and form a continuous sterile tissue, clavate to cylindrical or fusoid, often rather irregular in shape, not clamped at the base, and measuring 14–35×5.5–14 μm. The basidia are mostly 2-spored (rarely 1, 3, or 4-spored), clavate, not clamped at the base, and measure 18–36×6–8 μm. The basidiospores are broadly elliptical to slightly ovate in face view, unilaterally flattened-elliptical to -ovate in side view, smooth, thick-or thin-walled, lacking a germ pore, dark brown in mass, and measure 6.1–9.2×4.6–7.0 μm.

BRIEF DESCRIPTION OF THE FIGURES

FIG. 1 illustrates the allelic variability of *Agaricus brunnescens* cultures from The Pennsylvania State University Mushroom Culture Collection and from commercial spawn makers.

FIG. 2 illustrates a strategy for confirmation of hybridization and subsequent hybrid evaluation in the common cultivated mushroom.

a. Selection from germ plasm bank of parental breeding stock with alternate electrophoretic types.

b. Dual culture of parental lines on agar plates.

c. Selection of possible hybrid mycelium from interaction zone.

d. Culture of selection in liquid medium.

e. Electrophoretic confirmation of hybrid; types 1 and 2=parental lines; type 3=hybrid (note "extra" band); type 4=mix only of parental lines.

f. Production of spawn from confirmed hybrids for spawning compost.

g. Selection among different hybrid lines for desirable traits.

FIG. 3 is a photograph showing two forms of the mushroom plants of the present invention.

TABLE 1

Alleles possessed by the parental lines used to derive homokaryotic breeding stock for hybrid production

| Line No. | BIOCHEMICAL LOCI Gpt | Mpi | Pep-LLL-1 | Pep-LLL-2 | Adh | Aat |
|---|---|---|---|---|---|---|
| 232 | 100/165 | ∅[a] | 100/115 | 100/100 | 100/149 | 81/100 |
| 266 | 100/139 | ∅ | 100/115 | 100/111 | 100/165 | 81/100 |

[a]No activity

TABLE 2

Alleles possessed by homokaryotic breeding stock for hybrid production

| Line No. | BIOCHEMICAL LOCI Gpt | Mpi | Pep-LLL-1 | Pep-LLL-2 | Adh | Aat |
|---|---|---|---|---|---|---|
| 232–58 | 165 | ∅[a] | 115 | 100 | 100 | 81 |
| 266–324 | 139 | ∅ | 100 | 111 | 100 | 100 |

[a]No activity

TABLE 3

Alleles possessed by novel hybrid as a result of crossing homokaryotic breeding stock

| Line No. | BIOCHEMICAL LOCI Gpt | Mpi | Pep-LLL-1 | Pep-LLL-2 | Adh | Aat |
|---|---|---|---|---|---|---|
| BB32 (Hybrid) | 139/165 | ∅[a] | 100/115 | 100/111 | 100/100 | 81/100 |

[a]No activity

TABLE 4

Mushroom yield in lbs/ft$^2$ for crops 82-18 and 82-24 grown at The Mushroom Research Center of The Pennsylvania State University.

| Line # | Crop # 82-18 | 82-24 |
|---|---|---|
| 266 (parent 1) | 1.86 a* | 1.81 a* |
| BB32 ($F_1$ hybrid) | 1.54 b | 1.57 b |
| 348 (check) | 1.53 b | 1.32 c |
| BB32/1169 ($F_2$ hybrid) | 1.51 b | 1.52 bc |
| Moonlite TM (check) | 1.22 c | 1.22 d |
| 232 (parent 2) | 1.02 d | 1.31 cd |

*Means followed by the same letter within the same column are not significantly different based on the Waller-Duncan K-Ratio T-Test at P = 0.05.

TABLE 5

Mushroom size in grams/mushroom for crops 82-18 and 82-14 grown at The Mushroom Research Center of The Pennsylvania State University.

| Line # | Crop # 82-18 | 82-24 |
|---|---|---|
| BB32 ($F_1$ hybrid) | 7.30 a* | 6.68 a* |
| 232 (parent 2) | 7.29 a | 5.38 b |
| Moonlite TM (check) | 6.82 ab | 5.10 bc |
| 348 (check) | 6.67 b | 4.64 c |
| BB32/1169 ($F_2$ hybrid) | 6.41 b | 6.20 b |

TABLE 5-continued

Mushroom size in grams/mushroom for crops 82-18 and 82-14 grown at The Mushroom Research Center of The Pennsylvania State University.

| Line # | Crop # 82-18 | 82-24 |
|---|---|---|
| 266 (parent 1) | 5.35 c | 5.14 bc |

*Means followed by the same letter within the same column are not significantly different based on the Waller-Duncan K-Ratio T-Test at P = 0.05.

What is claimed is:

1. A new and distinct variety of mushroom plant substantially as shown and described characterized particularly as to novelty by its greater productivity and yield when compared to two commercially available lines, 348 and Moonlite TM and by its unique electrophoretic isozyme phenotype.

* * * * *